United States Patent [19]

Gastaud

[11] Patent Number: 4,544,555
[45] Date of Patent: Oct. 1, 1985

[54] 3,20-DIKETO, 6-METHYL, 17-ALPHA-HYDROXY 19-NORPREGNA 4,6-DIENE, ITS ESTERS AND THE USES THEREOF

[76] Inventor: Jean M. Gastaud, 3 avenue Prince Pierre, Monte Carlo, Monaco

[21] Appl. No.: 424,350

[22] Filed: Sep. 27, 1982

Related U.S. Application Data

[63] Continuation of Ser. No. 144,064, Apr. 28, 1980, abandoned, and a continuation-in-part of Ser. No. 577,009, May 13, 1975.

[51] Int. Cl.$^4$ .............................. C07J 5/00; C07J 7/00
[52] U.S. Cl. .................................................. 260/397.4
[58] Field of Search ....................................... 260/397.4

[56] References Cited

FOREIGN PATENT DOCUMENTS 2522533  12/1975  Fed. Rep. of Germany ... 260/397.4
1515284   6/1978  United Kingdom ............. 260/397.4

OTHER PUBLICATIONS

Chem. Abstracts, vol. 84 (1976), Par. 122,148(j).

*Primary Examiner*—Elbert L. Roberts
*Attorney, Agent, or Firm*—Gifford, VanOphem, Sheridan, Sprinkle & Nabozny

[57] ABSTRACT

A novel 3,20-diketo, 6-methyl, 17-alpha hydroxy 19-norpregna-4,6-diene is disclosed, along with a method for its production from 17-alpha-hydroxy 19-nor-progesterone acetate. The 17-alpha acetic ester, and the 17-alpha saturated or unsaturated aliphatic carboxylic acid esters (having up to 11 carbon atoms) of the compound, are also disclosed. The compound and its derivatives are useful in the treatment of luteal deficiency, hyperestrogenic or hyperandrogenic conditions, and seborrhea, either simple or complicated with acne.

18 Claims, No Drawings

3,20-DIKETO, 6-METHYL, 17-ALPHA-HYDROXY 19-NORPREGNA 4,6-DIENE, ITS ESTERS AND THE USES THEREOF

CROSS REFERENCE TO RELATED APPLICATION

This application is a continuation of copending Ser. No. 144,064, filed Apr. 28, 1980, now abandoned; and a continuation-in-part of Ser. No. 577,009, filed May 13, 1975, now abandoned.

FIELD OF THE INVENTION agent.

SUMMARY OF THE PRESENT INVENTION

This invention relates to a new steroid of the series of compounds derived from 17-alpha-hydroxy,19-nor-pregna 4,6-diene 3,20-dione, and its use in human therapeutics by the oral, perlingual, transcutaneous, rectal or parenteral route, as a progestational, anti-estrogen, anti-androgen and pituitary-suppressing agent.

According to the invention, this new compound is 3,20-diketo, 6-methyl, 17-alpha hydroxy,19-nor-pregna 4,6-diene, having the formula (I)

and its 17-alpha esters, such as the 17-alpha-acetoxy ("Compound II" hereafter) and 17-alpha hexanoyloxy ("compound III" hereafter) esters.

The new compound of the invention can be prepared starting from 3,20-diketo, 17-alpha-acetoxy, 19-nor-pregna 4,6-diene in the following sequence:

A—The starting material is methoxylated by ethyl-orthoformate in acid conditions into the 3-methoxy derivative.

B—Said 3-methoxy derivative is formylated using Vilmeier's reagent (PO Cl 3 + dimethyl formamide) into the 3-methoxy, 6-formyl derivative.

C—This product is reduced (C1) by sodium borohydride to a non isolated intermediary, which, in acid conditions, leads (C2) to 6-methylene, 17-alpha-acetoxy,19-nor-progesterone which is isomerised in the presence of palladium charcoal, to 3,20-diketo, 6-methyl, 17-alpha-acetoxy,19-nor-pregna-4,6-diene, which is an ester of the compound (I) of the invention and therefore comprised within the invention.

D—This ester is hydrolyzed by methanolic potassium to compound I, and can be further esterified, more specifically, to the 17-alpha-hexanoyloxy derivative, which is also comprised within the invention.

This sequence can be illustrated by the following scheme:

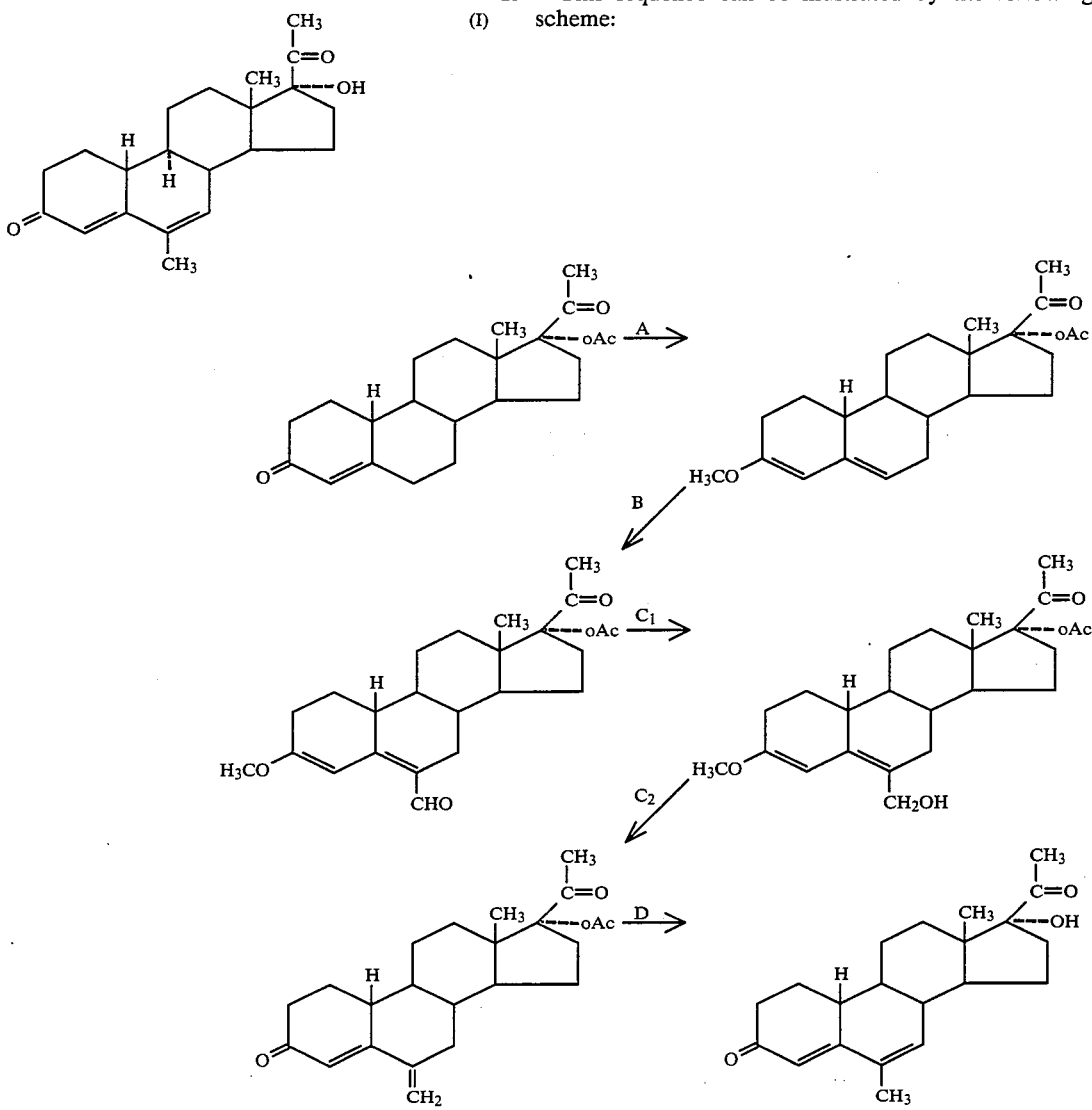

17-alpha-hydroxy 19-nor-progesterone acetate used as starting material in this process, has been described by C. Djerassi et al. (J. Am. Chem. Soc. 1954,76,6210).

According to another embodiment modification of this process an enol ether is used which must be formylated in position 6 according to the method (B) using the reagent formed from the action of phosphorus oxychloride (POCl3) on dimethylformamide (D.M.F.) (Belgian Pat. No. 610 054). After reduction and dehydration to a 6-methylene derivative (C2), the compound obtained is isomerised to a 6-methyl derivative (D), according to a method that has already been reported (U.S. Pat. Nos. 3,117,966; 3,705,181; N.L. 6,911,649).

According to a still further embodiment of the present invention, the intermediary 6-methylene derivative can also be prepared by the action of N,N-dimethylformaldimmonium trifluoroacetate (J. Am. Chem. Soc. 1968, 90, 5622) on 3-methoxy, 17-alpha-acetoxy,20-keto, 19-norpregna-3,5-diene (Upjohn, Belgian Pat. BE No. 759,143).

The 6-methyl,17-alpha-hydroxy, 3,20-diketo,19-nor-pregna-4,6-diene derivative of the invention (I) is obtained by hydrolysis of the acetoxy derivative in the presence of methanolic potassium. There can be prepared this compound (I) esters, comprised within the invention, by action of an acid anhydride in the presence of perchloric acid in a solvent such as chloroform. An acid chloride can also be used in pyridine or in a solvent such as chloroform in the presence of triethylamine or dimethylamino-4-pyridine.

DETAILED DESCRIPTION OF THE PREFERRED EMBODIMENTS OF THE PRESENT INVENTION

This process will be illustrated by the following non limitative examples:

EXAMPLE NO. 1

Preparation of 3-methoxy,17-alpha-acetoxy,20-keto,19-nor-pregna-3,5-diene (step A)

17 ml ethyl orthoformate and 1 g p-toluenesulphonic acid were added to a suspension of 16.5 g of 17-alpha-acetoxy, 19-nor-progesterone in 250 ml dioxane. After shaking for 3 hours at room temperature, 6 ml pyridine were added; the reaction mixture was then shaken for a further 2 hours and slowly poured into 2 liters of water. The precipitate was dried, washed and dried.

After crystallisation in methanol containing 1% pyridine, crystals (M.P. 212°–214° C.) of a compound corresponding to a centesimal analysis of $C_{23}H_{32}O_4$ were obtained.

EXAMPLE NO. 2

Preparation of 6-formyl, 3-methoxy,17-alpha-acetoxy,20-keto,19-nor-pregna-3,5-diene (step B)

A mixture of 6.5 ml phosphorus oxychloride and 55 ml dimethylformamide was slowly added to a solution of 9 g of the product obtained in step A in 100 ml of anhydrous dimethylformamide.

After stirring for 1 hour and 30 minutes, the reaction mixture was poured into 1.5 liters of a saturated aqueous solution of sodium bicarbonate. After extraction with chloroform, 11 g of the crude product were obtained which were used as such for the remaining part of the synthesis.

EXAMPLE NO. 3

Preparation of 6-methylene,17-alpha-acetoxy,19-nor-progesterone (step C)

1 g sodium borohydride was added during a period of 15 minutes at room temperature to 9 g of the product of step B, in a solution of 90 ml methanol. After extraction with chloroform, the crude product was directly added to 100 ml methanol to which 10 ml of 1 N HCl were added.

The mixture was shaken for 30 minutes at room temperature and poured into 1 liter of water; the crystalline precipitate (5.5 g) was then dried. M.P. 195° C. Centesimal analysis: $C_{23}H_{30}O_4$.

EXAMPLE NO. 4

Preparation of 3,20-diketo,6-methyl,17-alpha-acetoxy,19-nor-pregna-4,6-diene (step D)

600 mg sodium acetate and 1.2 g palladium charcoal were added to 1.2 g of the product of step C, in 240 ml ethanol. The solution was refluxed for 1 hour and 30 minutes. After extraction and crystallisation in methanol, crystals were obtained (60% yield). M.P. 178° C. Centesimal analysis: $C_{23}H_{30}O_4$.

EXAMPLE NO. 5

Preparation of 3,20-diketo,6-methyl,17-alpha-hydroxy,19-nor-pregna-4,6-diene (Compound I)

1 g of the product of step D was dissolved in 40 ml ethanol containing 20% water and 0.5 g potassium. After one hour at 60° C., the reaction mixture was extracted. The product obtained crystallised in methanol. M.P. 204°–205° C. Centesimal analysis: $C_{21}H_{28}O_3$.

| N.M.R. spectrum (60 megacycles/sec.; CDCl3; T.M.S. $\delta$ = 0) | | |
| --- | --- | --- |
| CH3 at $C_{(20)}$ | singlet | at 136 Hz |
| CH3 at $C_{(6)}$ | large singlet | at 111 Hz |
| CH3 at $C_{(13)}$ | singlet | at 56 Hz |

EXAMPLE NO. 6

Preparation of 3,20-diketo,6-methyl,17-alpha-hexanoyloxy,19-nor-pregna-4,6-diene (ester of Compound I)

1 g of Compound I was dissolved in 25 cc chloroform; a solution of 3 cc hexanoic anhydride and 200 mg p-toluenesulphonic acid were added. The reaction mixture was heated to its reflux temperature under a nitrogen atmosphere for 3 hours. Half of the solvent was then distilled, and 15 cc ethanol and 0.2 cc concentrated hydrochloric acid were added. This mixture was refluxed for 1 hour under nitrogen. This was done with the aim of hydrolysing the enol ester formed at position $C_{(3)}$. The reaction mixture was then diluted with ice water and brought to pH 8 with sodium hydroxide. After extraction, 3 g oil were obtained which crystallised from hexane after purification by silica column chromatography. Melting point: 132° C.

This substance is characterized by an infra-red spectrum having absorption bands at 1735,1715,1655,1620,1575 $cm^{-1}$.

CLINICAL RESULTS

Compound (I) is new; its progestational properties, which are potential, are revealed by esterification of the alcohol function in position 17α, with the result that it considerably increases the bio-availability of the compound and renders it liposoluble.

The acetic ester of compound I ("compound II" hereafter) was mentioned in an English patent, No. 1,231,296, amongst twenty-one other compounds derived from the same chemical reaction, but without having been identified by any of its usual physical and chemical characteristics and without any allusion made to its biological properties or to its therapeutic applications.

It is precisely these therapeutic applications which are the object of this invention: compound II is a powerful progestational, active by oral and injectable routes and with no side-effects.

The hexanoic ester of compound I ("compound III") is only one example amongst other possible esters of fatty acids with a relatively long chain, such as: butyrate, heptanoate, decanoate, undecanoate, cyclo-pentylpropionate, cyclo-hexylpropionate, etc. . . . This ester, administered by injectable route, possesses particularly prolonged activity, lasting about ten days; orally, its effectiveness is less.

Biologic activity

To fill the normal conditions of non-limitative therapeutic use, a synthetic progestational must simultaneously possess pseudo-gestational, gestational, anti-estrogenic, anti-androgenic and pituitary-inhibiting properties, and have no undesirable hormonal side-effects (androgenic, estrogenic, cortisol-like, or aldosterone-like) nor noxious effects on the glucide metabolism nor on the liver functions.

Although a number of known ideas can be applied to obtain a steroid with good pseudo-gestational effects, and even to avoid some of the unwanted effects, there is, however, no known relation between structure and activity enabling the simultaneous elimination of all negative effects.

Now (and herein lies one of the main originalities of the compounds according to the present invention), these compounds possess all the necessary properties but none of the adverse properties of various known progestationals, including those with relatively close chemical structures.

The studies briefly reported hereafter prove the originality of the claimed compounds, as defined above.

All these studies were performed using the acetic ester of compound I ("compound II") for the following reasons:

First, the activity of this ester being practically identical by the oral and parenteral routes, it was possible to study the compound after administration by both routes in a large number of cases.

Second, with one exception, the reference progestationals used for oral comparisons were all acetates: medroxyprogesterone acetate, chlormadinone acetate, megestrol acetate, norethisterone acetate.

Third, the biologic activities of "compound II" can never be fundamentally different from those of the other esters of "compound I".

The following table lists the known progestationals to which "compound II" was compared. Opposite each is its abbreviation, the route(s) by which it was administered, as well as the mean daily dose at which it is active in human therapeutics (the human dose enables a more adequate interpretation of the experimental results reported hereafter).

|  | Abbreviation | possible routes of administration | mean daily human dose |
|---|---|---|---|
| progesterone | P | i.m. | 20–40 mg |
| Derivatives of 17α-OH progesterone | | | |
| 17α-acetate of 19-nor-pregna,4,6-diene 3,20-dione | Compound II | p.o. (i.m.) | 2,5 mg |
| medroxyprogesterone acetate | MPA | p.o. (i.m.) | 20–40 mg |
| chlormadinone acetate | CLAC | p.o. | 2–5 mg |
| megestrol acetate | MEGAC | p.o. | 15–60 mg |
| Derivatives of 19-nor-testosterone | | | |
| norethisterone acetate | NORAC | p.o. | 10–20 mg |
| norethynodrel | NOREL | p.o. | 2,5–5 mg (as contraceptive combination) |

A—Investigation for properties characteristic of a therapeutically useful progestational 1/Pseudo-gestational activity (a) By the general route: C. CLAUBERG's method (Zentr. Gynaäkol., 1930,54,2757–2770), modified by M. K. Mac PHAIL (J. Physiol.London, 1934,83,145–156).

Subcutaneously, in immature female rabbits, "compound II" possesses analogous activity to that of subcutaneous progesterone: $ED_{50}$ for index 2: 1.3 mg/animal/5 days versus 1.2 mg/animal/5 days for progesterone.

Orally, "compound II" is 5 times more active than MPA and 1.5 times more active than MEGAC.

(b) In intra-uterine administrations: D. A. Mac GINTY et al.'s test (Endocrinology, 1939,24,829–832) in immature rabbits.

"Compound II" is twice as active as injectable progesterone, but three times less active than MPA; despite this, the interest of this test is to have shown that "compound II" is able to accede directly to the specific progesterone receptors, to the uterine mucosa and muscle, like progesterone, and this already demonstrates its real gestational properties.

2/True progestational activity (a) Determination of the decidual reponse in spayed rats after oral treatment; E. B. ASTWOOD's method (J. Endocrinol., 1939,1,49–55).

Contrary to NOREL and NORAC, "compound II" provokes a decidual response and the effects are dose-related. The failure of both reference products is due to their parallel estrogenic properties.

(b) Maintenance of gestation in spayed rats: method derived from M. X. ZARROW et al.'s techniques (Experimental Endocrinology, 1964, p. 100–101, Academic Press, New York), from T. MIYAKE (Steroids, 1963,2,749–763) and Z. S. MADJEREK (International Encyclopedia of Pharmacology and Therapeutics, M. TAUSK, Edit., 1971, section 48, vol. I, 291–318).

Compared with MPA, "compound II" possesses analogous s.c. activity though weaker per os (on the other hand, MPA cannot be used during pregnancy, amongst other reasons, because of its androgenic activities, of which "compound II" is devoid).

3/Anti-estrogenic activity (a) Anti-cornifying activity in young female rats by the oral route: method derived from L. J. LERNER et al.'s technique (Endocrinology, 1958,63:295–318).

"Compound II" is approximately twice less active than CLAC (which, however, is devoid of anti-uterotrophic effects; see below).

(b) Subcutaneous and oral anti-uterotrophic activity in young mice: R. A. EDGREN et alia's method (Endocrinology, 1959,65: 265–272).

Subcutaneously, "compound II" has an activity equal to that of MPA; orally, it is half as active as MPA, but clearly more active than MEGAC (in this test CLAC was completely inactive).

4/Pituitary-inhibiting activity (a) Inhibition of the remaining ovary, after unilateral ovariectomy in rats: D. L. PETERSON et al.'s method (J. Endocrinol., 1964,29: 255–262).

Subcutaneously, the test-product possesses an important effect, quantitatively analogous to that of MPA and P; orally, it is more active than MEGAC and a little less than MPA.

(b) Pituitary-inhibiting effects using the parabiosis technique in rats: C. E. HALL's method (in "Methods of Animal Experimentation", W. I. GAY, Ed., 1965, vol. II, p. 223–249, Academic Press, New-York).

"Compound II" was far less active than MPA with this method, as was CLAC. The difference with the preceding test can be explained by direct gonadal inhibition by "compound II", property which cannot be revealed by parabiosis.

(c) Effects on ovulation

α/In adult, normal, female rats treated subcutaneously: J. W. EVERETT's method (Endocrinology, 1948,43: 389–405), "compound II" inhibits ovulation at least four times more than P (0.25 mg/animal/day versus 1 mg/animal/day, respectively).

β/In immature female rats, stimulated by PMS: R. V. GALLOW and M. X. ZARROW's method (Endocrinology 1970,86: 296–304) and C. E. Mac CORMACK and R. K. MEYER's method (General and Comparative Endocrinology, 1963,3:300–307).

Like progesterone and all reference progestationals of the 17α-OH-P family, "compound II" stimulates ovulation in this test; its mechanism is hypothetical.

What should be remembered from these two series of studies is that "compound II" behaves like a real progestational.

5/Anti-androgenic activity

R. I. DORFMAN's method (in "Methods in Hormone Research", 1962, vol. II, p.315–323, Academic Press, New-York); study in immature rats.

Contrary to MPA, which is inactive, subcutaneously "compound II" is a powerful inhibitor on both specific receptors (prostate and seminal vesicles). This important activity is confirmed orally, "compound II" being superior to CLAC, which is considered by all authors as the most anti-androgenic progestational.

B—Investigation for parallel, unwanted hormonal properties 1/Androgenic activity In immature male rats: A. G. HILGAR and D. J. HUMMEL's method ("The Androgenic and Myogenic Evaluation of Steroids and Other Compounds", in "Endocrine Bioassay Data", 1967, issue I, p.41–42, Department of Health, Education and Welfare), "compound II" shows no androgenic activity, either subcutaneously or orally, even up to a dose of 10 mg/animal/day. It should be well noted that in the same test, P and MPA cause stimulation of the specific receptors, weakly but undeniably.

2/Estrogenic activity (a) Cornifying activity

In young, spayed rats: method inspired from that of C. W. EMMENS (in "Methods in Hormone Research", R. I. DORFMAN, Ed., 1962, vol. II, p. 59–111, Academic Press, New-York), "compound II" is completely inert, like the three other reference progestationals of the same chemical family.

(b) Uterotrophic activity

In immature mice: method described by A. G. HILGAR et al. ("The Uterotrophic Evaluation of Steroids and Other Compounds", Assay 2 in "Endocrine Bioassay Data", 1968, Issue 3, 1–2, Department of Health, Education and Welfare), "compound II" was also inert, contrary to two progestagens derived from nandrolone, NOREL and NORAC, of well-known activity in this respect.

3/Cortisol-like activity (a) Thymolytic activity in adrenalectomised male rats, treated subcutaneously and orally according to R. K. MEYER et al.'s technique (Proc. Soc. Exp. Biol. Med., 1953,84: 624–627), described by A. G. HILGAR et al. ("The Thymolytic Evaluation of Steroids and Other Compounds", Assay 8, in "Endocrine Bioassay Data", 1968, Issue 2, 1–3, Department of Health, Education and Welfare).

"Compound II" does not cause atrophy of the thymus, even at the enormous s.c. dose of 24 mg/animal, and orally, 80 mg. In this test, MPA is weakly, though clearly, active, its thymolytic effect being roughly 5% that of cortisol.

(b) The effect of "Compound II" on the pituitary-adrenal axis was determined by: decrease in weight of the adrenals, reduction in circulating levels of cortisol and the histology of the adrenals of ovariectomised rats treated orally: R. L. ELTON et al.'s method (Proc.-Soc.Exp.Biol.Med., 1960,103: 175–177).

Several reference progestationals belonging to the same chemical family, such as MPA and MEGAC, possess cortisol-like effects, manifested by the decrease in weight of the adrenals, histological and histochemical modification of the gland and decrease in circulating cortisol levels. On the contrary, "compound", according to the doses, does not modify, or else cause an increase in the weight of the adrenals, as well as in the plasma levels of cortisol; these effects are confirmed histologically.

C—Investigation for parallel, unwanted, non-hormonal properties

1/Liver function

The study consisted in the clearance test of bromesulphtalein (B.S.P.), introduced intra-veinously to adult male rats, treated orally with the test-progestationals (technique derived from G. BOURDON et al., Rev. Int. Hépatol, 1958,8: 473–477).

"Compound II" does not modify either elimination time of B.S.P. or the quantities elliminated.

2/Carbohydrate metabolism

The study consisted in the determination of glucose tolerance test by intra-veinous route in male adult rabbits, previously treated with the test-products either orally or intra-veinously, under conditions described by P. BECK (Diabetes, 1969,18: 146–152) for monkeys; the glucose plasma levels were determined continuously, according to O. BLAMPIN et al.'s method (C.R. Soc.-Biol.Paris, 1962, 156: 346–348).

Progestationals are generally considered diabetogenic because they decrease glucide tolerance by increasing insulin secretion and encouraging peripheral resistance to this hormone. Such an effect was found in the controls treated with MPA.

"Compound II", on the contrary, at the weak dose (1 mg/kg/day) does not cause any modification in comparison with the controls; at the highest dose (5 mg/kg/day), on the contrary, it causes acceleration of the decrease in glycaemia, as if it stimulated insulin secretion, without developing peripheral resistance to insulin; "compound II", in this respect, behaves like P and CLAC.

3/Water and the electrolyte metabolism

The study consisted in determining hydric diuresis and excretion of sodium and potassium in adult, male, adrenalectomised rats, kept alive with desoxycorticosterone acetate (DOCA) and receiving a sodium chloride supplement.

The effects of the test-products, administered either subcutaneously or orally, were determined according to variations in volume and urinary pH, and urinary levels of sodium and potassium.

The mineral-corticotropic or anti-mineral-corticotropic activity was calculated with a series of equations. Physiologically, DOCA reduces the urinary volume and sodium elimination; this effect is suppressed by spironolactone at a dose of 1 mg/animal; it is increased by MPA at the dose of 30 mg/animal subcutaneously and 30 mg/animal orally. On the contrary, and up to the dose of 30 mg/animal (subcutaneously and orally), "compound II" does not modify, in any direction, hydric and/or sodium diuresis. It should be noted that in this test, P showed only a weak, spironolactone-like effect.

D—Originality of the particular biological outline of the compounds claimed by this invention Orally active progestationals, presently available throughout the world, belong to two large chemical families: 1/nortestosterone (or nandrolone); 2/17α-hydroxyprogesterone (17α-OH-P).

Among the results of the experimental investigations summarised above, some show where the difference lie, between the compounds claimed by the present invention and the existing progestationals. These differences are listed below.

1/It is known that the compounds of the nandrolone family all possess unwanted side-effects, some of which are even incompatible with normal conditions of prolonged use: estrogenic and androgenic activities, liver toxicity, reduction in the carbohydrates tolerance, decrease in hydro-sodium diuresis, etc.

Progestationals derived from nandrolone are rarely used in current endocrine gynaecology because their side-effects.

The compounds claimed by the present invention are fundamentally distinguishable from nandrolone derivatives, not only because of their real pseudo-gestational and gestational activities, but also because they have no androgenic, estrogenic, cortisol-like, anti-diuretic, diabetogenic, or liver-toxic effects.

2/The group of 17α-OH-P derivatives is represented in therapeutics by three main compounds: MPA, CLAC, MEGAC.

(a) The compounds claimed by the present invention are distinguished from medroxyprogesterone acetate (MPA) by:
their pseudo-gestational activities, which are five times more important;
the absence of any androgenic properties;
their direct gonad-inhibiting effects added to their pituitary-inhibiting effects;
the absence of any cortisol-like effect: atrophy of the adrenals, thymolytic and anti-inflammatory;
by complete neutrality with regards the hydro-sodium metabolism;
their capacity to improve glucide tolerance by stimulating insulin secretion and sensitivity of the peripheral tissues to insulin.

(b) The compounds claimed by the present invention are distinguished from chlormadinone acetate (CLAC) by:
the absence of cortisol-like effects (which CLAC, as well as MPA, possesses);
stronger anti-androgenic, gonad-inhibiting and anti-uterotrophic activities.

(c) The compounds claimed are also distinguished from megestrol acetate (MEGAC) by:
any androgenic effect;
the absence of any cortisol-like effect (anatomic and histologic atrophy of the cortico-adrenals, with decrease in the blood levels of cortisol);
twice as powerful anti-uterotrophic activities;
one and a half times stronger pseudo-gestationals activities.

These qualitative and quantitative elements which differentiate the biologic outline of the claimed compounds from that of MEGAC are particularly demonstrative of the individuality of "compound I" according to the invention, and its esters, since, of all the progestationals derived from 17α-OH-P, MEGAC possesses the closest chemical structure to those of compounds I and II.

Therapeutic applications

The compounds relating to the invention are useful in human therapeutics as progestationals, pituitary inhibitors, anti-estrogens, anti-androgens, anti-seborrhoeics and inhibitors of endometrium, mammary and/or prostata hypertrophy or hyperplasia.

According to the therapeutic aim, the clinical history and the physico-chemical particularities of each of the compounds related to this invention, the compounds can be administered by one of the following routes: intramuscular, oral, perlingual, percutaneous, rectal or vaginal.

The following are four types of examples of appropriate therapeutical preparations:

(1) Injectable ampoules containing 50 to 150 mg/ml of "compound II" or "III" of the invention, in a pharmaceutically acceptable solvent, would by used for the intramuscular treatment of any form of chronic luteal insufficiency or hyperestrogenism, such as menometrorrhagia, uterine fibromyoma, mastodynia, endometriosis, prostata hypertrophy and other such scientifically accepted indications of progestagens. The dosage is to be adapted to each of the indications; it could vary from 50 mg to 2 g per treatment or per month.

(2) Tablets or soft capsules destined for the oral or perlingual routes, with an appropriate and pharmaceutically acceptable excipient and containing 1 to 10 mg of "compound II" would preferentially be administered for the gynaecological forms of luteal insufficiency: irregular menses, secondary amenorrhoea or meno-metrorrhagia, prostata hypertrophy and/or other conditions accepted as indications for progestagens, at daily doses varying from 1 to 10 mg.

(3) Rectal or vaginal suppositories containing from 20 to 50 mg of compounds "I", "II" or "III" would be more appropriate for the rectal treatment of prostata hypertrophy for example or for the vaginal treatment of some hyperestrogenic conditions, such as endometriosis or endometrial hyperplasia, at daily doses varying from 20 to 50 mg.

(4) Solutions, emulsions, gels, creams or ointments containing per ml or per gram from 5 to 25 mg of one of compounds "I", "II" or "III", in a pharmaceutically acceptable excipient would be destined for the local treatment of seborrhoea (simple or complicated with acne) at a dosage varying from 5 to 25 mg per day.

What I claim is:

1. The 3,20-diketo, 6-methyl,17-alpha hydroxy 19-nor-pregna-4,6-diene.

2. The 17-alpha acetic ester of the compound of claim 1.

3. The 17-alpha saturated or unsaturated aliphatic carboxylic acid esters, with up to 11 carbon atoms, of the compound of claim 1.

4. A method for the intramuscular treatment of luteal deficiency, or hyperestrogenic or hyperandrogenic conditions, which comprises administering the compound of claim 1 by injection from injectable ampuls containing 50 to 150 mg/ml of the compound in a pharmaceutically acceptable solvent.

5. A method for the oral or perlingual treatment of luteal deficiency, or hyperestrogenic or hyperandrogenic conditions, which comprises administering the compound of claim 1 by oral introduction of tablets or soft capsules containing one to ten mg of the compound in a pharmaceutically acceptable excipient, further comprising a total daily dosage from one to ten mg.

6. A method for the intracavital treatment of luteal deficiency, or hyperestrogenic or hyperandrogenic conditions, which comprises administering the compound of claim 1 by insertion of vaginal or rectal suppositories containing 20 to 50 mg of the compound in a pharmaceutically acceptable excipient, further comprising a total daily dosage from 20 to 50 mg.

7. A method for the transcutaneous treatment of seborrhoea, either simple or complicated with acne, which comprises administering the compound of claim 1 by transcutaneous application of a solution, emulsion, gel, cream, or ointment containing 5 to 25 mg of the compound in pharmaceutically acceptable excipient, further comprising a total daily dosage from 5 to 25 mg.

8. A method for the intramuscular treatment of luteal deficiency, or hyperestrogenic or hyperandrogenic conditions, which comprises administering the compound of claim 2 by injection from injectable ampuls containing 50 to 150 mg/ml of the compound in a pharmaceutically acceptable solvent.

9. A method for the oral or perlingual treatment of luteal deficiency, or hyperestrogenic or hyperandrogenic conditions, which comprises administering the compound of claim 2 by oral introduction of tablets or soft capsules containing one to ten mg of the compound in a pharmaceutically acceptable excipient, further comprising a total daily dosage from one to ten mg.

10. A method for the intracavital treatment of luteal deficiency, or hyperestrogenic or hyperandrogenic conditions, which comprises administering the compound of claim 2 by insertion of vaginal or rectal suppositories containing 20 to 50 mg of the compound in a pharmaceutically acceptable excipient, further comprising a total daily dosage from 20 to 50 mg.

11. A method for the transcutaneous treatment of seborrhoea, either simple or complicated with acne, which comprises administering the compound of claim 2 by transcutaneous application of a solution, emulsion, gel, cream, or ointment containing 5 to 25 mg of the compound in a pharmaceutically acceptable excipient, further comprising a total daily dosage from 5 to 25 mg.

12. A method for the intramuscular treatment of luteal deficiency, or hyperestrogenic or hyperandrogenic conditions, which comprises administering the compound of claim 3 by injection from injectable ampuls containing 50 to 150 mg/ml of the compound in a pharmaceutically acceptable solvent.

13. A method for the oral or perlingual treatment of luteal deficiency, or huperestrogenic or hyperandrogenic conditions, which comprises administering the compound of claim 3 by oral introduction of tablets or soft capsules containing one to ten mg of the compound in a pharmaceutically acceptable excipient, further comprising a total daily dosage from one to ten mg.

14. A method for the intracavital treatment of luteal deficiency, or hyperestrogenic or hyperandrogenic conditions, which comprises administering the compound of claim 3 by insertion of varginal or rectal suppositories containing 20 to 50 mg of the compound in a pharmaceutically acceptable excipient, further comprising a total daily dosage from 20 to 50 mg.

15. A method for the transcutaneous treatment of seborrhoea, either simple or complicated with acne, which comprises administering the compound of claim 3 by transcutaneous application of a solution, emulsion, gel, cream, or ointment containing 5 to 25 mg of the compound in a pharmaceutically acceptable excipient, further comprising a total daily dosage from 5 to 25 mg.

16. A process for preparing a 17α-hydroxy-19-norpregna-4,6-dien-3,20-dione derivative of the formula wherein R is selected from the group consisting of hydrogen, acetyl, and saturated and unsaturated acyl groups of up to 11 carbon atoms, which comprises:

(a) reacting 17α-acetoxy-3,20-diketo-19-norpregna-3,5-diene with ethyl orthoformate in acid medium to give 3-methoxy-17α-acetoxy-20-keto-19-norpregna-3,5-diene;

(b) reacting said compound with phosphorus oxychloride and dimethylformamide to give 6-formyl-3-methoxy-17α-acetoxy-20-keto-19-norpregna-3,5-diene;

(c) reducing said compound with sodium borohydride to give 6-hydroxymethyl-3-methoxy-17α-acetoxy-20-keto-19-norpregna-3,5-diene;

(d) reacting said nonisolated compound with acid to give 6-methylene-17α-acetoxy-19-norprogesterone;

(e) isomerizing said compound in the presence of palladium on charcoal to give 3,20-diketo-6-methyl-17α-acetoxy-19-norpregna-4,6-diene;

(f) hydrolyzing said compound with potassium methylate to form 3,20-diketo-6-methyl-17α-hydroxy-19-norpregna-4,6-diene; and (g) esterifying said compound with an appropriate esterfying reagent.

17. A process according to claim 11, wherein the enol ether of step (a) is formylated at the $C_6$-position using a reagent formed from phosphorus oxychloride and dimethylformamide to produce the compound of step (b), and after reduction and dehydration, forming the 6-methylene derivative of step (e).

18. A process according to claim 11, wherein the intermediary 6-methylene derivative of step (d) is prepared by reaction of N,N-dimethylformaldiammonium trifluoroacetate with 3-methoxy-17α-acetoxy-20-keto-19-norpregna-3,5-diene.

* * * * *

UNITED STATES PATENT AND TRADEMARK OFFICE
CERTIFICATE OF CORRECTION

PATENT NO. : 4,544,555
DATED : October 1, 1985
INVENTOR(S) : JEAN M. GASTAUD

It is certified that error appears in the above-identified patent and that said Letters Patent are hereby corrected as shown below:

Title page, field 63, under "Related U.S. Application Data", line 3, after "May 13, 1975" insert --, now abandoned--.

Title page, appropriate fields, please insert: --The term of this patent subsequent to June 30, 1996, has been disclaimed.--; and --[30] Foreign Application Priority Data
May 21, 1974 [UK] United Kingdom        22656/74--.

Column 1, line 7 (in the first heading), delete "APPLICATION" and insert --APPLICATIONS--, line 10, after "INVENTION" delete "agent."

line 11, delete the title "SUMMARY OF THE PRESENT INVENTION".

UNITED STATES PATENT AND TRADEMARK OFFICE
CERTIFICATE OF CORRECTION

PATENT NO. : 4,544,555

DATED : October 1, 1985

INVENTOR(S) : JEAN M. GASTAUD

It is certified that error appears in the above-identified patent and that said Letters Patent are hereby corrected as shown below:

Column 1, after line 17, insert the title --SUMMARY OF THE PRESENT INVENTION--.

Column 2, line 11, delete "POC13" and insert --$POCl_3$--.

line 21, delete "methanolic" and insert --methylated--.

Column 3, line 3, delete "76" and insert --$\underline{76}$--.

line 4, delete "modification".

line 8, delete "(POC13)" and insert --($POCl_3$)--.

line 18, delete "maldimmonium" and insert --maldiammonium--.

line 19, delete "90" and insert --$\underline{90}$--.

line 25, delete "methanolic" and insert --methylated--.

UNITED STATES PATENT AND TRADEMARK OFFICE
CERTIFICATE OF CORRECTION

PATENT NO. : 4,544,555
DATED : October 1, 1985
INVENTOR(S) : JEAN M. GASTAUD

It is certified that error appears in the above-identified patent and that said Letters Patent are hereby corrected as shown below:

Column 3, line 49, delete "dried," (first occurrence) and insert --filtered,--.

Column 4, line 30, after "potassium", insert --hydroxide--;

line 32, after "obtained" insert --was-- line 47, delete "cc", insert --ml--;

line 68, delete "position 17$\alpha$," and insert --the 17$\alpha$ position--.

Column 6, line 25, delete "Gynaakol" and insert --Gynakol--.

line 25, delete "54" and insert --$\underline{54}$--.

line 26, delete "83" and insert --$\underline{83}$--.

line 36, delete "24" and insert --$\underline{24}$--.

line 46, delete "reponse" and insert --response--.

UNITED STATES PATENT AND TRADEMARK OFFICE
CERTIFICATE OF CORRECTION

PATENT NO. : 4,544,555
DATED : October 1, 1985
INVENTOR(S) : JEAN M. GASTAUD

It is certified that error appears in the above-identified patent and that said Letters Patent are hereby corrected as shown below:

Column 6, line 48, delete "1" and insert --$\underline{1}$--.

line 57, delete "2" and insert --$\underline{2}$--.

line 68, delete "63:" and insert --$\underline{63}$,--.

Column 7, line 6, delete "65:" and insert --$\underline{65}$,--.

line 14, delete "29:" and insert --$\underline{29}$,--.

line 22, delete "New-York" and insert --New York--.

line 31, delete "43:" and insert --$\underline{43}$,--.

line 36, delete "86:" and insert --$\underline{86}$,--.

line 38, delete "3:" and insert --$\underline{3}$,--.

line 48, delete "New-York" and insert --New York--.

line 56, after "properties" delete "1/Androgenic activity".

UNITED STATES PATENT AND TRADEMARK OFFICE
CERTIFICATE OF CORRECTION

PATENT NO. : 4,544,555
DATED : October 1, 1985
INVENTOR(S) : JEAN M. GASTAUD

It is certified that error appears in the above-identified patent and that said Letters Patent are hereby corrected as shown below:

Column 7, after line 56, insert a new paragraph heading --1/Androgenic activity--.

Column 8, line 20, delete "84:" and insert --84,--.

line 34, after "Proc." delete "-".

line 35, delete "103:" and insert --103,--.

line 41, after "compound" and before the quotation mark, insert --II--.

line 53, delete "8:" and insert --8,--.

line 61, delete "18:" and insert --18,--.

line 64, after "Soc." delete "-".

line 65, delete "156:" and insert --156,--.

UNITED STATES PATENT AND TRADEMARK OFFICE
CERTIFICATE OF CORRECTION

PATENT NO. : 4,544,555
DATED : October 1, 1985
INVENTOR(S) : JEAN M. GASTAUD

It is certified that error appears in the above-identified patent and that said Letters Patent are hereby corrected as shown below:

Column 9, line 13, after "and" insert --the--.

line 40, delete "summarised" and insert --summarized--; same line, delete "difference" and insert --differences--.

line 51, after "because" insert --of--.

Column 10, line 24, delete "pseudo-gestationals" and insert --pseudo-gestational--.

line 51, delete "by" and insert --be--.

Column 12, line 15 (claim 13, line 2), delete "huperestrogenic" and insert --hyperestrogenic--.

line 24, (claim 14, line 4), delete "varginal" and insert --vaginal--.

line 36, (claim 16, line 2), delete "dien" and insert --diene--.

UNITED STATES PATENT AND TRADEMARK OFFICE
CERTIFICATE OF CORRECTION

PATENT NO. : 4,544,555
DATED : October 1, 1985
INVENTOR(S) :

It is certified that error appears in the above-identified patent and that said Letters Patent are hereby corrected as shown below:

Column 12, after line 36, (claim 16, after line 2), insert the following formula:

--

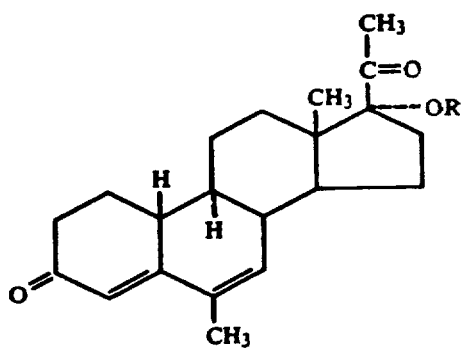

--.

line 64 (claim 16, 27th printed line), delete "esterfying" and insert --esterifying--.

line 65 (claim 17, line 1), delete "11" and insert --16--.

UNITED STATES PATENT AND TRADEMARK OFFICE
CERTIFICATE OF CORRECTION

PATENT NO. : 4,544,555

DATED : October 1, 1985

INVENTOR(S) : JEAN M. GASTAUD

It is certified that error appears in the above-identified patent and that said Letters Patent are hereby corrected as shown below:

Column 13, line 3, (claim 18, line 1), delete "11" and insert --16--.

Signed and Sealed this

Fourth Day of November, 1986

[SEAL]

Attest:

DONALD J. QUIGG

*Attesting Officer*   *Commissioner of Patents and Trademarks*